(12) United States Patent
Fujihara

(10) Patent No.: US 7,727,553 B2
(45) Date of Patent: Jun. 1, 2010

(54) ORAL PREPARATIONS WITH FAVORABLE DISINTEGRATION CHARACTERISTICS

(75) Inventor: Kazuyuki Fujihara, Takatsuki (JP)

(73) Assignee: Dainippon Sumitomo Pharma Co., Ltd., Osaka-Shi, Osaka (JP)

( * ) Notice: Subject to any disclaimer, the term of this patent is extended or adjusted under 35 U.S.C. 154(b) by 803 days.

(21) Appl. No.: 10/381,036

(22) PCT Filed: Sep. 14, 2001

(86) PCT No.: PCT/JP01/07983

§ 371 (c)(1),
(2), (4) Date: Mar. 21, 2003

(87) PCT Pub. No.: WO02/24166

PCT Pub. Date: Mar. 28, 2002

(65) Prior Publication Data

US 2004/0028741 A1    Feb. 12, 2004

(30) Foreign Application Priority Data

Sep. 22, 2000   (JP)   .............................. 2000-288234

(51) Int. Cl.
*A61K 9/14* (2006.01)
(52) U.S. Cl. .................. 424/489; 424/452; 424/457; 424/458; 424/468; 424/470
(58) Field of Classification Search .............. 424/400, 424/464, 465, 489, 469, 451, 452, 457, 458, 424/459, 461, 468, 470, 471, 474
See application file for complete search history.

(56) References Cited

U.S. PATENT DOCUMENTS

| | | | |
|---|---|---|---|
| 5,532,372 A * | 7/1996 | Saji et al. ..................... 544/368 |
| 5,811,120 A | 9/1998 | Gibson et al. | |
| 5,958,453 A * | 9/1999 | Ohno et al. .................. 424/465 |
| 5,972,383 A | 10/1999 | Gibson et al. | |
| 5,994,348 A | 11/1999 | Ku et al. | |
| 6,440,450 B1 * | 8/2002 | Han et al. .................... 424/439 |

FOREIGN PATENT DOCUMENTS

| | | |
|---|---|---|
| EP | 860169 | 8/1998 |
| EP | 860169 A2 | 10/1998 |
| JP | 61-148114 A | 7/1986 |
| JP | 2000016930 | 1/2000 |
| JP | 2000-86503 A | 3/2000 |
| JP | 2000-86509 A | 3/2000 |
| WO | WO-95/17168 | 6/1995 |
| WO | WO-99/32092 A1 | 7/1999 |
| WO | WO-99/47126 | 9/1999 |
| WO | WO-00/64416 | 11/2000 |

* cited by examiner

*Primary Examiner*—D L Jones
(74) *Attorney, Agent, or Firm*—Birch, Stewart, Kolasch & Birch, LLP

(57) ABSTRACT

The present invention provides oral preparations with good disintegration containing a slightly water-soluble active ingredient, which comprise a mixture of a solid formed product (e.g. a granule) and a second disintegrant wherein said solid formed product comprises a slightly water-soluble active ingredient, a first disintegrant and a water-soluble excipient which is formed by using a water-soluble polymer binder; or comprises a solid formed product prepared from a slightly water-soluble active ingredient, a disintegrant and a sugar alcohol by using a water-soluble polymer binder. When orally administered, these oral preparations exhibit excellent dissolution characteristics of the active ingredient in the digestive tract, and further, these preparations can show equivalent dissolution profile even at different amounts of the active ingredient, and thus enable the selection of the most suitable medicament for each patient, which makes these preparations highly useful in the clinical field.

11 Claims, No Drawings

ORAL PREPARATIONS WITH FAVORABLE DISINTEGRATION CHARACTERISTICS

This application is the national phase under 35 U.S.C. §371 of PCT International Application No. PCT/JP01/07983 which has an International filing date of Sep. 14, 2001, which designated the United States of America.

TECHNICAL FIELD

The present invention relates to an oral preparation with good disintegration, which comprises a slightly water-soluble component as an active ingredient. More particularly, the present invention relates to pharmaceutical preparations for oral administration, especially tablets, containing a slightly water-soluble component as an active ingredient, which have equivalent dissolution profile of the active ingredient even at different contents of the active ingredient. Further, the present invention relates to a pharmaceutical preparation for oral administration, especially tablets, containing a slightly water-soluble component as an active ingredient, which show a rapid dissolution of the active ingredient even though the amount of the active ingredient therein is varied in the range of several mg to several tens of mg, for example, in the range of 5 mg to 20 mg or in the range of 5 mg to 40 mg, and further these preparations show equivalent dissolution profile in the same ratio of components.

BACKGROUND ART

In order to secure the bioequivalence when a pharmaceutical preparation having different amounts is administered at the same dose, there was issued "Guideline for Bioequivalence testing of Oral Solid Dosage Forms with Different Content" (Notification No. 64 of the Evaluation and Licensing Division, PMSD dated Feb. 14, 2000), by which it has been required that a pharmaceutical preparation having different amounts should be equivalent in dissolution profile in test solutions such as buffers of pH 1.2, 3.0 to 5.0 and 6.8 (which correspond to the pH values of the stomach, the intestine and the oral cavity, respectively), water, and saline solution, etc.

For medicaments showing a good solubility in water, it is easy to prepare such a preparation having equivalent dissolution profile even in different amounts due to their water solubility. On the contrary, for medicaments containing as an active ingredient a slightly water-soluble compound, it has been difficult to prepare a pharmaceutical preparation having equivalent dissolution profile even in different amounts, because such an active ingredient shows low affinity to water, etc.

DISCLOSURE OF INVENTION

An object of the present invention is to provide a pharmaceutical preparation for oral administration containing as an active ingredient a slightly water-soluble compound, which can rapidly release the active ingredient therefrom and can show equivalent dissolution profile even in different amounts of said active ingredient. Especially, the object of the present invention is to provide a pharmaceutical preparation for oral administration with increased amount of the active ingredient, which can show equivalent dissolution profile to that when multiple tablets having a low content of the active ingredient are administered, and can release a slightly water-soluble active ingredient therefrom at a desired concentration.

The present inventor has intensively studied in order to achieve the above objects, and has found that pharmaceutical preparations prepared by the following processes showed a good disintegration, and can show a rapid dissolution profile regardless of the contents of the active ingredient, by releasing the active ingredient therefrom at a desired concentration, and further can show equivalent dissolution profile, and found that such pharmaceutical preparations meet the desired purposes, and finally has accomplished the present invention.

(1) A process of making a preparation comprising a step of preparing a solid formed product (e.g., granule) from a slightly water-soluble active ingredient and a mixture of a first disintegrant and a water-soluble excipient with a water-soluble polymer binder, and a step of mixing the resultant with a second disintegrant.

(2) A process of making a preparation comprising a step of preparing a solid formed product from a mixture of a slightly water-soluble active ingredient, a first disintegrant and a water-soluble excipient with a water-soluble polymer binder, and a step of mixing the resultant with a second disintegrant.

(3) A process of making a preparation comprising a step of preparing a solid formed product from a slightly water-soluble active ingredient and a mixture of a first disintegrant and a sugar alcohol with a water-soluble polymer binder.

(4) A process of making a preparation comprising a step of preparing a solid formed product from a mixture of a slightly water-soluble active ingredient, a first disintegrant and a sugar alcohol with a water-soluble polymer binder.

BEST MODE FOR CARRYING OUT THE INVENTION

The present invention will be explained in more detail hereinafter.

According to the present invention, oral preparations in the following various embodiments are provided.

(1) An oral preparation with good disintegration, which comprises a mixture of a granule and a second disintegrant, said granule being obtained by granulating with spraying an aqueous suspension containing a slightly water-soluble active ingredient and a water-soluble polymer binder to a mixture of a water-soluble excipient and a first disintegrant.

(2) The oral preparation with good disintegration according to the above (1), which is in the form of a tablet.

(3) An oral preparation with good disintegration, which comprises a mixture of an active ingredient-containing layered composite and a second disintegrant, said layered composite being made by setting a slightly water-soluble active ingredient-containing layer onto an internal layer consisting of a water-soluble excipient and a first disintegrant via a layer of a water-soluble polymer binder.

(4) An oral preparation with good disintegration, which comprises a mixture of a granule and a second disintegrant, said granule being obtained by granulating with spraying an aqueous solution of a water-soluble polymer binder to a mixture of a slightly water-soluble active ingredient, a water-soluble excipient and a first disintegrant.

(5) The oral preparation with good disintegration according to the above (4), which is in the form of a tablet.

(6) An oral preparation with good disintegration, which comprises a mixture of an active ingredient-containing granule and a second disintegrant, said granule being obtained by combining a slightly water-soluble medicament, a water-soluble excipient and a first disintegrant each other by a water-soluble polymer binder.

(7) An oral preparation with good disintegration, which comprises a granule obtained by granulating with spraying an aqueous suspension containing a slightly water-soluble active ingredient and a water-soluble polymer binder to a mixture of a sugar alcohol and a first disintegrant.

(8) The oral preparation with good disintegration according to the above (7), which is in the form of a tablet.

(9) An oral preparation with good disintegration, which comprises an active ingredient-containing layered composite, said layered composite being made by setting a slightly water-soluble active ingredient-containing layer onto the internal layer consisting of a sugar alcohol and a first disintegrant via a layer of a water-soluble polymer binder.

(10) An oral preparation with good disintegration, which comprises a granule obtained by granulating with spraying an aqueous solution of a water-soluble polymer binder to a mixture of a slightly water-soluble active ingredient, a sugar alcohol and a first disintegrant.

(11) The oral preparation with good disintegration according to the above (10), which is in the form of a tablet.

(12) An oral preparation with good disintegration, which comprises an active ingredient-containing granule, said granule being obtained by combining a slightly water-soluble medicament, a sugar alcohol and a first disintegrant each other by a water-soluble polymer binder.

(13) The oral preparation with good disintegration according to any one of the above (1) to (12), wherein the slightly water-soluble active ingredient has a solubility of not more than 0.1 mg/ml at either pH 1.0, 3.0 to 5.0, or 6.8.

(14) The oral preparation with good disintegration according to any one of the above (1) to (12), wherein the average particle diameter of the slightly water-soluble active ingredient is in the range of about 0.5 to 5 µm.

(15) The oral preparation with good disintegration according to any one of the above (1), (2), (3), (4), (5) and (6), wherein the water-soluble excipient is a saccharide or a sugar alcohol.

(16) The oral preparation with good disintegration according to any one of the above (1), (2), (3), (4), (5) and (6), wherein the water-soluble excipient is a sugar alcohol.

(17) The oral preparation with good disintegration according to any one of the above (1), (2), (3), (4), (5) and (6), wherein the water-soluble excipient is a saccharide and a sugar alcohol.

(18) The oral preparation with good disintegration according to any one of the above (1), (2), (3), (4), (5) and (6), wherein the water-soluble excipient is one or more members selected from lactose, sucrose, fructo-oligosaccharide, paratinose, glucose, maltose, hydrogenated maltose, maltotetraose, fructose, isomerized lactose, lactitol, honey sugar, D-sorbitol, D-mannitol, maltitol, erythritol, and xylitol.

(19) The oral preparation with good disintegration according to any one of the above (1), (2), (3), (4), (5) and (6), wherein the water-soluble excipient is one or more members selected from D-sorbitol, D-mannitol, erythritol, and xylitol.

(20) The oral preparation with good disintegration according to any one of the above (7), (8), (9), (10), (11) and (12), wherein the sugar alcohol is one or more members selected from D-sorbitol, D-mannitol, erythritol, and xylitol.

(21) The oral preparation with good disintegration according to any one of the above (1), (2), (3), (4), (5) and (6), which comprises one or more water-soluble excipients selected from D-sorbitol, D-mannitol, erythritol, and xylitol, and further comprises one or more water-soluble excipients selected from lactose, sucrose, fructo-oligosaccharide, paratinose, glucose, maltose, hydrogenated maltose, maltotetraose, fructose, lactulose, lactitol and honey sugar.

(22) The oral preparation with good disintegration according to any one of the above (7), (8), (9), (10), (11) and (12), which comprises one or more sugar alcohols selected from D-sorbitol, D-mannitol, erythritol, and xylitol, and further comprises one or more water-soluble excipients selected from lactose, sucrose, fructo-oligo-saccharide, paratinose, glucose, maltose, hydrogenated maltose, maltotetraose, fructose, lactulose, lactitol and honey sugar.

(23) The oral preparation with good disintegration according to any one of the above (1), (2), (3), (4), (5) and (6), wherein the water-soluble excipient has an average particle diameter in the range of about 10 µm to 150 µm.

(24) The oral preparation with good disintegration according to any one of the above (7), (8), (9), (10), (11) and (12), wherein the sugar alcohol has an average particle diameter in the range of about 10 µm to 150 µm.

(25) The oral preparation with good disintegration according to any one of the above (1) to (12), wherein the first disintegrant is selected from corn starch, micro-crystalline cellulose, low substituted hydroxypropyl-cellulose, carmellose, carmellose calcium, carmellose sodium, croscarmellose sodium, carboxymethyl starch sodium and crosspovidone.

(26) The oral preparation with good disintegration according to any one of the above (1) to (12), wherein the water-soluble polymer binder is selected from hydroxy-propylcellulose, hydroxypropylmethylcellulose, polyvinyl-pyrrolidone, polyvinyl alcohol, agar, starch, dextrin and gelatin.

(27) The oral preparation with good disintegration according to any one of the above (1), (2), (3), (4), (5) and (6), wherein the second disintegrant is one or more members selected from lactose, anhydrous dibasic calcium phosphate, dibasic calcium phosphate, microcrystalline cellulose, low substituted hydroxypropylcellulose, carmellose, carmellose calcium, carmellose sodium, croscarmellose sodium, carboxymethyl starch sodium and crosspovidone.

(28) The oral preparation with good disintegration according to any one of the above (2), (5), (8) and (11), wherein the compression hardness is in the range of about 50 to 200 N.

(29) The oral preparation with good disintegration according to the above (1) or (2), wherein the second disintegrant is contained in a ratio of 20 to 1200 w/w % (by weight) to the weight of the granule obtained by granulating with spraying an aqueous suspension containing a slightly water-soluble active ingredient and a water-soluble polymer binder to a mixture of an excipient and a first disintegrant.

(30) The oral preparation with good disintegration according to the above (4) or (5), wherein the second disintegrant is contained in a ratio of 20 to 1200 w/w (by weight) to the weight of the granule obtained by granulating with spraying an aqueous solution of a water-soluble polymer binder to a mixture of a slightly water-soluble active ingredient, an excipient and a first disintegrant.

(31) The oral preparation with good disintegration according to any one of the above (1), (2), (3), (4), (5) and (6), wherein the amount of the water-soluble excipient is in the range of about 250 to 2000% by weight (w/w %, hereinafter the same) to the weight of the slightly water-soluble active ingredient.

(32) The oral preparation with good disintegration according to any one of the above (7), (8), (9), (10), (11) and (12), wherein the amount of the sugar alcohol is in the range of about 250 to 2000% by weight (w/w %, hereinafter the same) to the weight of the slightly water-soluble active ingredient.

(33) The oral preparation with good disintegration according to any one of the above (1) to (12), wherein the amount of the first disintegrant is in the range of about 5 to 300% by weight to the weight of the slightly water-soluble active ingredient.
(34) The oral preparation with good disintegration according to any one of the above (1) to (12), wherein the amount of the water-soluble polymer binder is in the range of about 6 to 80% by weight to the weight of the slightly water-soluble active ingredient.
(35) The oral preparation with good disintegration according to any one of the above (1) to (12), wherein the amount of the water-soluble polymer binder is in the range of about 1 to 10% by weight to the total weight of said preparation.
(36) The oral preparation with good disintegration according to any one of the above (1) to (12), wherein the amount of the water-soluble polymer binder is in the range of about 1 to 5% by weight to the total weight of said preparation.
(37) A granule, which is obtained by granulating with spraying an aqueous suspension containing a slightly water-soluble active ingredient and a water-soluble polymer binder to a mixture of a water-soluble excipient and a first disintegrant.
(38) A slightly water-soluble active ingredient-containing granule, which is obtained by adding a water-soluble polymer binder to a powdery mixture consisting of a water-soluble excipient, a first excipient and a slightly water-soluble active ingredient and combining them each other.
(39) A granule, which is obtained by granulating with spraying an aqueous suspension containing a slightly water-soluble active ingredient and a water-soluble polymer binder to a mixture of a sugar alcohol and a first disintegrant.
(40) A slightly water-soluble active ingredient-containing granule, which is obtained by adding a water-soluble polymer binder to a powdery mixture consisting of a sugar alcohol, a first disintegrant and a slightly water-soluble active ingredient and combining them each other.
(41) The oral preparation with good disintegration according to any one of the above (1) to (40), wherein the slightly water-soluble active ingredient is N-[4-[4-(1,2-benzisothiazol-3-yl)-1-piperazinyl]-(2R,3R)-2,3-tetra-methylenebutyl]-(1'R,2'S,3'R,4'S)-2,3-bicyclo[2.2.1]-heptanedicarboximide hydrochloride.

The "slightly water-soluble active ingredient" includes slightly soluble compounds having a low solubility in water, especially compounds having a solubility of not more than about 0.1 mg/ml at pH 1.0, 3.0-5.0 and 6.8, these pH values corresponding to the pH values of the stomach, the intestine and the oral cavity, respectively. A concrete example thereof is N-[4-[4-(1,2-benzisothiazol-3-yl)-1-piperazinyl]-(2R, 3R)-2,3-tetramethylenebutyl]-(1'R, 2'S, 3'R, 4'S)-2,3-bicyclo[2.2.1]heptanedicarboximide hydrochloride of the following formula:

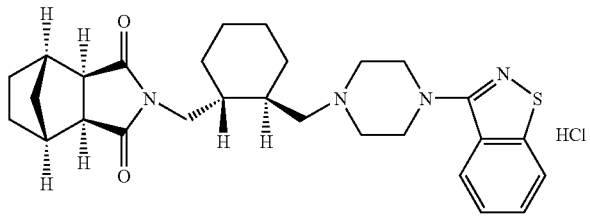

(hereinafter, referred to as Compound 1) (cf. Japanese Patent No. 2800953). Compound 1 has been known to exhibit a psychotropic effect, and it is useful as an agent for treatment of schizophrenia, etc.

In addition, these slightly water-soluble active ingredients are preferably finely milled, and the average particle diameter thereof is, for example, in the range of about 0.5 to 5 μm.

The "water-soluble polymer binder" includes, for example, hydroxypropylcellulose, hydroxypropylmethylcellulose, polyvinylpyrrolidone, polyvinyl alcohol (partially saponificated one), pullulan, starch, dextrin, gelatin, etc., and preferable ones are hydroxypropyl-cellulose, hydroxypropylmethylcellulose, polyvinyl-pyrrolidone, and polyvinyl alcohol (partially saponificated one). These water-soluble polymer binders may be used alone, or two or more thereof may be used together.

The "first disintegrant" includes, for example, corn starch, microcrystalline cellulose, low substituted hydroxypropyl-cellulose, carmellose, carmellose calcium, carmellose sodium, croscarmellose sodium, carboxymethyl starch sodium, crosspovidone, etc. These first disintegrants may be used alone or two or more thereof may be used together. The average particle diameter of these first disintegrants is, for example, in the range of about 5 to about 75 μm, and preferable first disintegrant is ones having an average particle diameter in the range of about 5 to about 75 μm, wherein the ratio of particles having a particle diameter of more than 75 μm is not more than 5% to the total.

The "second disintegrant" includes, for example, lactose, anhydrous dibasic calcium phosphate, dibasic calcium phosphate, microcrystalline cellulose, magnesium aluminometasilicate, synthesized hydrotalcite, synthesized aluminum silicate, low substituted hydroxypropyl cellulose, carmellose, carmellose calcium, carmellose sodium, cros-carmellose sodium, carboxymethyl starch sodium, cross-povidone, etc. Preferable second disintegrant is, for example, lactose, anhydrous dibasic calcium phosphate, dibasic calcium phosphate, microcrystalline cellulose, low substituted hydroxypropyl cellulose, carmellose, carmellose calcium, carmellose sodium, croscarmellose sodium, carboxymethyl starch sodium, and crosspovidone. These second disintegrants may be used alone, or two or more thereof may be used together.

The average particle diameter of the second disintegrant is, for example, in the range of about 5 to about 500 μm, preferably in the range of about 30 to 350 μm.

The "water-soluble excipient" includes, for example, a sugar alcohol and a saccharide. Specific examples are saccharides such as lactose, sucrose, fructo-oligo-saccharide, paratinose, glucose, maltose, hydrogenated maltose, maltotetraose, fructose, lactulose, lactitol, honey sugar, and sugar alcohols such as D-sorbitol, D-mannitol, maltitol, erythritol, and xylitol. These water-soluble excipients may be used alone, or one or more thereof may be used together.

Even when the amount of the slightly water-soluble active ingredient is substantially changed, for example, even when it is changed within the range of 5 mg to 40 mg, the oral preparation shall show a rapid dissolution of said active ingredient as well as equivalent dissolution profile, and the water-soluble excipients preferable for preparing such oral preparation are, for example, sugar alcohols such as D-sorbitol, D-mannitol, erythritol, xylitol, etc. In these cases, a saccharide such as lactose, sucrose, fructo-oligosaccharide, paratinose, glucose, maltose, hydrogenated maltose, maltotetraose, fructose, lactulose, lactitol, honey sugar, etc. may simultaneously be contained in said oral preparation.

When orally administered, the oral preparation of the present invention can release a slightly water-soluble active ingredient rapidly and can show equivalent dissolution profile regardless of the amounts of the active ingredient therein to give a desired serum concentration thereof. The oral preparations of the present invention may include various dosage forms such as pills, granules, fine granules, tablets, capsules, etc.

The oral preparations of the present invention may be prepared by a conventional method depending on desired dosage forms. For instance, the present preparations may be prepared by the following processes.

Preparation Method 1

(1) Preparation of an aqueous solution of a water-soluble polymer binder:

A water-soluble polymer binder is dissolved in purified water, during which the temperature is, for example, in the range of about 20° C. to 90° C., preferably in the range of about 20° C. to 70° C. The amount of the water-soluble polymer binder is, for example, in the range of about 1 to 20% by weight, preferably in the range of about 2 to 8% by weight, to the weight of the purified water.

(2) Preparation of an aqueous suspension containing a water-soluble polymer binder and a slightly water-soluble active ingredient:

A slightly water-soluble active ingredient is dispersed and suspended in the aqueous water-soluble polymer binder solution obtained in the above (1), for example, at a temperature of about 20° C. to about 90° C., preferably at a temperature of about 20° C. to 40° C.

The amount of the water-soluble polymer binder is, for example, in the range of about 3 to about 200% by weight, preferably about 6 to about 80% by weight, to the weight of the slightly water-soluble active ingredient.

The slightly water-soluble active ingredient is preferably finely milled, and the average particle diameter thereof is, for example, in the range of about 0.5 to 5 µm.

(3) Mixing and granulation of the active ingredient-containing aqueous suspension with a first disintegrant:

A water-soluble excipient and a first disintegrant are charged into a fluid bed granulator, and thereto is sprayed the aqueous suspension containing a water-soluble polymer binder and a slightly water-soluble active ingredient obtained in the above (2), and the mixture is granulated.

This granulation step is carried out, for example, at a temperature for supplying air in the range of about 50° C. to 90° C., preferably about 60° C. to 80° C. The granulation is carried out, for example, for about 30 minutes to 180 minutes, preferably for about 40 minutes to 150 minutes.

The apparatus for granulation is, for example, ones classified into fluid bed granulation and roto granulation, and preferable one is a fluid bed granulator, a roto fluid bed granulator, etc.

The amount of the water-soluble excipient is, for example, in the range of about 200 to about 2000% by weight, preferably in the range of about 250 to about 1200% by weight, to the weight of the slightly water-soluble active ingredient.

The amount of the first disintegrant is in the range of about 5 to 300% by weight, preferably in the range of about 30 to 150% by weight, to the weight of the slightly water-soluble active ingredient.

(4) Drying of the granule:

The above granule containing a slightly water-soluble active ingredient and a first disintegrant is dried either under reduced pressure or under atmospheric pressure. The drying is carried out in such a manner that the loss on dry measured by infrared moisture meter is, for example, within about 3% by weight, preferably within 2% by weight.

(5) Mixing of the dried granule and a second disintegrant:

The granule containing a slightly water-soluble active ingredient and a first disintegrant dried in the above (4) is then mixed with a second disintegrant. The mixing apparatus is, for example, ones classified into diffusion mixers (tumble mixers). If necessary, after mixing with said mixer, the mixture is milled with a mill classified into impact mills. The diffusion mixers (tumble mixers) are, for example, tumble blender, V blender, double cone, bin tumbler, etc. The impact mills are, for example, a hammer conventional mill, etc.

The amount of the second disintegrant is, for example, in the range of 20 to 1200 w/w % (weight ratio) to the weight of the granule obtained by granulating with spraying the aqueous suspension of a slightly water-soluble active ingredient and a water-soluble polymer binder to a mixture of a first disintegrant and a water-soluble excipient.

(6) Blending of a lubricant:

The above mixture of the granule and the second disintegrant may be compressed without further components, but preferably compressed in admixture with a lubricant.

The lubricant may be blended by adding it into the mixture of the above (5). The mixing apparatus is, for example, ones classified into diffusion mixers (tumble mixers), such as tumble blender, V blender, double cone, bin tumbler, etc.

The lubricant is, for example, magnesium stearate, talc, hydrogenated oil, stearic acid, calcium stearate, glyceryl behenate, sodium stearylfumarate, etc.

The amount of the lubricant is, for example, in the range of 0.3 to 3% by weight, preferably in the range of about 0.5 to 1.5% by weight, to the total weight of the tablet.

(7) Compression:

The above mixture is compressed in a conventional manner to give tablets.

The compression apparatus is preferably ones classified into tablet press.

The compression hardness is, for example, in the range of about 50 to 200 N.

(8) Film Coating:

The tablets obtained above may be subjected to film coating, if necessary. The coating apparatus is ones classified into coating pans, preferably ones classified into perforated coating system.

The coating agent is, for example, a mixture of a base material (e.g., hydroxypropylmethylcellulose, hydropropylcellulose, polyvinylpyrrolidone, etc.) and a plasticizer (e.g., polyethylene glycol, propylene glycol, triacetine, triethyl citrate, glycerin, glycerin fatty acid ester, polyethylene glycol, etc.). If necessary, an additive such as titanium oxide or mannitol may be added therein.

(9) Drying:

The tablets obtained above are dried. The drying is carried out either under reduced pressure or under atmospheric pressure in such a manner that the loss on dry measured by infrared moisture meter is, for example, within about 3% by weight, preferably within 2% by weight.

Preparation Method 2

(1) Preparation of an aqueous solution of a water-soluble polymer binder:

A water-soluble polymer binder is dissolved in purified water, during which the temperature is, for example, in the range of about 20° C. to 90° C., preferably in the range of about 20° C. to 70° C. The amount of the water-soluble polymer binder is, for example, in the range of about 1 to 20% by weight, preferably in the range of about 2 to 8% by weight, to the weight of the purified water.

(2) Preparation of an active ingredient-containing granule:

A slightly water-soluble active ingredient, a water-soluble excipient and a first disintegrant are charged into a fluid bed granulator, and thereto is sprayed the aqueous solution of a water-soluble polymer binder obtained in the above (1), and the mixture is granulated.

The granulation step is carried out, for example, at a temperature for supplying air in the range of about 50° C. to 90° C., preferably about 60° C. to 80° C. The granulation is carried out, for example, for about 30 minutes to 180 minutes, preferably for about 40 minutes to 150 minutes.

The apparatus for granulation is, for example, ones classified into fluid bed granulation and roto granulation, and preferable one is a fluid bed granulator, a roto fluid bed granulator, etc.

The amount of the water-soluble excipient is, for example, in the range of about 200 to about 2000% by weight, preferably in the range of about 250 to about 1200% by weight, to the weight of the slightly water-soluble active ingredient.

The slightly water-soluble active ingredient is preferably finely milled, and the average particle diameter thereof is, for example, in the range of about 0.5 to 5 µm.

The amount of the first disintegrant is, for example, in the range of about 5 to 300% by weight, preferably in the range of about 30 to 150% by weight, to the weight of the slightly water-soluble active ingredient.

(3) Drying of the granule:

The above granule is dried either under reduced pressure or under atmospheric pressure. The drying is carried out in such a manner that the loss on dry measured by infrared moisture meter is, for example, within about 3% by weight, preferably within 2% by weight.

(4) Mixing of the dried granule and a second disintegrant:

The granule dried in the above (3) is mixed with a second disintegrant. The mixing apparatus is, for example, ones classified into diffusion mixers (tumble mixers). If necessary, after mixing by said mixers, the mixture is milled by a mill classified into impact mills. The diffusion mixers (tumble mixers) are, for example, tumble blender, V blender, double cone, bin tumbler, etc. The impact mills are, for example, a hammer conventional mill, etc.

The amount of the second disintegrant is, for example, in the range of 20 to 1200 w/w % to the weight of the granule obtained by granulating with spraying the aqueous suspension of a slightly water-soluble active ingredient and a water-soluble polymer binder to a water-soluble excipient.

(5) Blending of a lubricant:

The above mixture of the granule and the second disintegrant may be compressed without further components, but preferably compressed in admixture with a lubricant.

The lubricant may be blended by adding it into the mixture of the above (4). The mixing apparatus is, for example, ones classified into diffusion mixers (tumble mixers), such as tumble blender, V blender, double cone, bin tumbler, etc.

The lubricant is, for example, magnesium stearate, talc, hydrogenated oil, stearic acid, calcium stearate, glyceryl behenate, sodium stearylfumarate, etc. The amount of the lubricant is, for example, in the range of 0.3 to 3% by weight, preferably in the range of about 0.5 to 1.5% by weight, to the total weight of the tablet.

(6) Compression:

The above mixture is compressed in a conventional manner to give tablets.

The compression apparatus is preferably ones classified into tablet press.

The compression hardness is, for example, in the range of about 50 to 200 N.

(7) Film Coating:

The tablets obtained above may be subjected to film coating, if necessary. The coating apparatus is one classified into coating pans, preferably ones classified into perforated coating system.

The coating agent is, for example, a mixture of a base material (e.g., hydroxypropylmethylcellulose, hydropropylcellulose, polyvinylpyrrolidone, etc.) and a plasticizer (e.g., polyethylene glycol, propylene glycol, triacetine, triethyl citrate, glycerin, glycerin fatty acid ester, polyethylene glycol, etc.). If necessary, an additive such as titanium oxide or mannitol may be added therein.

(8) Drying:

The tablets obtained above are dried. The drying is carried out either under reduced pressure or under atmospheric pressure in such a manner that the loss on dry measured by infrared moisture meter is, for example, within about 3% by weight, preferably within 2% by weight.

Preparation Method 3

(1) Preparation of an aqueous solution of a water-soluble polymer binder:

A water-soluble polymer binder is dissolved in purified water, during which the temperature is, for example, in the range of about 20° C. to 90° C., preferably in the range of about 20° C. to 70° C. The amount of the water-soluble polymer binder is, for example, in the range of about 1 to 20% by weight, preferably in the range of about 2 to 8% by weight, to the weight of the purified water.

(2) Preparation of an aqueous suspension containing a water-soluble polymer binder and a slightly water-soluble active ingredient:

A slightly water-soluble active ingredient is dispersed and suspended in the aqueous solution of a water-soluble polymer binder obtained in the above (1), during which the temperature is, for example, in the range of about 20° C. to about 90° C., preferably in the range of about 20° C. to 40° C.

The amount of the water-soluble polymer binder is, for example, in the range of about 3 to about 200% by weight, preferably in the range of about 6 to about 80% by weight, to the weight of the slightly water-soluble active ingredient.

The slightly water-soluble active ingredient is preferably finely milled, and the specific average particle diameter thereof is, for example, in the range of about 0.5 to 5 µm.

(3) Mixing and granulation of the active ingredient-containing aqueous suspension with a sugar alcohol and a first disintegrant:

A sugar alcohol and a first disintegrant are charged into a fluid bed granulator, and thereto is sprayed the aqueous suspension containing a water-soluble polymer binder and a slightly water-soluble active ingredient obtained in the above (2), and the mixture is granulated.

This granulation step is carried out, for example, at a temperature for supplying air in the range of about 50° C. to 90° C., preferably about 60° C. to 80° C. The granulation is carried out, for example, for about 30 minutes to 180 minutes, preferably for about 40 minutes to 150 minutes.

The apparatus for granulation is, for example, ones classified into fluid bed granulation and roto granulation, and preferable one is a fluid bed granulator, a roto fluid bed granulator, etc.

The amount of the sugar alcohol is, for example, in the range of about 200 to about 2000% by weight, preferably in the range of about 250 to about 1200% by weight, to the weight of the slightly water-soluble active ingredient.

The amount of the first disintegrant is in the range of about 5 to 300% by weight, preferably in the range of about 30 to 150% by weight, to the weight of the slightly water-soluble active ingredient.

(4) Drying of the granule:

The above granule containing a slightly water-soluble active ingredient and a first disintegrant is dried either under reduced pressure or under atmospheric pressure. The drying is carried out in such a manner that the loss on dry measured by infrared moisture meter is, for example, within about 3% by weight, preferably within 2% by weight.

(5) Blending of a lubricant:

The above granule may be compressed without further components, but preferably compressed in admixture with a lubricant.

The lubricant may be blended by adding it into the above granule. The mixing apparatus is, for example, ones classified into diffusion mixers (tumble mixers), such as tumble blender, V blender, double cone, bin tumbler, etc.

The lubricant is, for example, magnesium stearate, talc, hydrogenated oil, stearic acid, calcium stearate, glyceryl behenate, sodium stearylfumarate, etc.

The amount of the lubricant is, for example, in the range of 0.3 to 3% by weight, preferably in the range of about 0.5 to 1.5% by weight, to the total weight of the tablet.

(6) Compression:

The above mixture is compressed in a conventional manner to give tablets.

The compression apparatus is preferably ones classified into tablet press.

The compression hardness is, for example, in the range of about 50 to 200 N.

(7) Film Coating:

The tablets obtained above may be subjected to film coating, if necessary. The coating apparatus is ones classified into coating pans, preferably ones classified into perforated coating system.

The coating agent is, for example, a mixture of a base material (e.g., hydroxypropylmethylcellulose, hydropropylcellulose, polyvinylpyrrolidone, etc.) and a plasticizer (e.g., polyethylene glycol, propylene glycol, triacetine, triethyl citrate, glycerin, glycerin fatty acid ester, polyethylene glycol, etc.). If necessary, an additive such as titanium oxide or mannitol may be added therein.

(8) Drying:

The tablets obtained above are dried. The drying is carried out either under reduced pressure or under atmospheric pressure in such a manner that the loss on dry measured by infrared moisture meter is, for example, within about 3% by weight, preferably within 2% by weight.

Preparation Method 4

(1) Preparation of an aqueous solution of a water-soluble polymer binder:

A water-soluble polymer binder is dissolved in purified water, during which the temperature is, for example, in the range of about 20° C. to 90° C., preferably in the range of about 20° C. to 70° C. The amount of the water-soluble polymer binder is, for example, in the range of about 1 to 20% by weight, preferably in the range of about 2 to 8% by weight, to the weight of the purified water.

(2) Preparation of an active ingredient-containing granule:

A slightly water-soluble active ingredient, a sugar alcohol and a first disintegrant are charged into a fluid bed granulator, and thereto is sprayed the aqueous solution of water-soluble polymer binder obtained in the above (1), and the mixture is granulated.

This granulation step is carried out, for example, at a temperature for supplying air in the range of about 50° C. to 90° C., preferably about 60° C. to 80° C. The granulation is carried out, for example, for about 30 minutes to 180 minutes, preferably for about 40 minutes to 150 minutes.

The apparatus for granulation is, for example, ones classified into fluid bed granulation and roto granulation, and preferable one is a fluid bed granulator, a roto fluid bed granulator, etc.

The amount of the sugar alcohol is, for example, in the range of about 200 to about 2000% by weight, preferably in the range of about 250 to about 1200% by weight, to the weight of the slightly water-soluble active ingredient.

The slightly water-soluble active ingredient is preferably finely milled, and the specific average particle diameter is, for example, in the range of about 0.5 to 5 μm.

The amount of the first disintegrant is, for example, in the range of about 5 to 300% by weight, preferably in the range of about 30 to 150% by weight, to the weight of the slightly water-soluble active ingredient.

(3) Drying of the granule:

The above granule is dried either under reduced pressure or under atmospheric pressure. The drying is carried out in such a manner that the loss on dry measured by infrared moisture meter is, for example, within about 3% by weight, preferably within 2% by weight.

(4) Blending of a lubricant:

The above granule may be compressed without further components, but preferably compressed in admixture with a lubricant.

The lubricant may be blended by adding it into the above granule. The mixing apparatus is, for example, ones classified into diffusion mixers (tumble mixers), such as tumble blender, V blender, double cone, bin tumbler, etc.

The lubricant is, for example, magnesium stearate, talc, hydrogenated oil, stearic acid, calcium stearate, glyceryl behenate, sodium stearylfumarate, etc.

The amount of the lubricant is, for example, in the range of 0.3 to 3% by weight, preferably in the range of about 0.5 to 1.5% by weight, to the total weight of the tablet.

(5) Compression:

The above mixture is compressed to give tablets.

The compression apparatus is preferably ones classified into tablet press. The compression hardness is, for example, in the range of about 50 to 200 N.

(6) Film Coating:

The tablets obtained above may be subjected to film coating, if necessary. The coating apparatus is ones classified into coating pans, preferably ones classified into perforated coating system.

The coating agent is, for example, a mixture of a base material (e.g., hydroxypropylmethylcellulose, hydropropylcellulose, polyvinylpyrrolidone, etc.) and a plasticizer (e.g., polyethylene glycol, propylene glycol, triacetine, triethyl citrate, glycerin, glycerin fatty acid ester, polyethylene glycol, etc.). If necessary, an additive such as titanium oxide or mannitol may be added therein.

(7) Drying:

The tablets obtained above are dried. The drying is carried out either under reduced pressure or under atmospheric pressure in such a manner that the loss on dry measured by infrared moisture meter is, for example, within about 3% by weight, preferably within 2% by weight.

EXAMPLES

The present invention is illustrated by the following Examples, but should not be construed to be limited thereto.

Example 1

A. Formula of Film Coating (FC) Tablets (10 mg-tablet) Containing 10 mg of Compound 1:

Granules, uncoated tablets and FC tablets were successively prepared from the following components, the content of which is expressed by an amount contained in one tablet.

(a) Formula of granules:

TABLE 1

| Component | Content (mg) |
| --- | --- |
| Compound 1 | 10 |
| Lactose | 50 |
| Croscarmellose sodium | 6 |
| Polyvinyl alcohol | 1.2 |

(b) Formula of uncoated tablets:

TABLE 2

| Component | Content (mg) |
| --- | --- |
| Granule of the above (a) | 67.2 |
| Anhydrous dibasic calcium phosphate | 35 |
| Microcrystalline cellulose | 17 |
| Magnesium stearate | 0.8 |

(c) Formula of FC tablets

TABLE 3

| Component | Content (mg) |
| --- | --- |
| Uncoated tablets of the above (b) | 120 |
| Hydroxypropylmethylcellulose | 1.95 |
| Titanium oxide | 0.6 |
| Conc. glycerin | 0.45 |
| Carnauba wax | Trace |

B. Preparation Method:

(1) Preparation of a binding solution:

Polyvinyl alcohol (12 g) as a water-soluble polymer binder was dissolved in purified water (228 g), and Compound 1 (100 g) was dispersed and suspended therein to give a binding solution.

(2) Granulation:

Lactose (500 g) as a water-soluble excipient and croscarmellose sodium (60 g) as a first disintegrant were charged into a fluid bed granulator (Multiplex MP-01 manufactured by Pawrex Corporation), and the mixture was granulated by spray granulation under the following conditions using the binding solution obtained in the above (1) to give a granule of the formula (a).

Conditions for granulation:
  Temperature for supplying air: 70° C.
  Airflow: 50 m$^3$/hr
  Spray speed: 10 g/min.
  Diameter of spray nozzle: 1.2 mm
  Spray pressure: 1.0 kg/cm$^2$
  Gun position: the lower stand (3) Mixing of the granule and a second disintegrant:

To the granule obtained in the above (2) (537.6 g) were added microcrystalline cellulose (136 g) and anhydrous dibasic calcium phosphate (280 g) as second disintegrants, and the mixture was mixed by a compact V blender (manufactured by Tsutsui Rikagaku Kikai Co., Ltd.) at 40 rpm for 5 minutes. Subsequently, the mixture was further mixed by Fits Mill (manufactured by HOSOKAWAMICRON CORPORATION) (2350 rpm, knife, 16 mesh). After mixing, magnesium stearate (6.4 g) as a lubricant was added thereto and blended (40 rpm, 5 minutes).

(4) Compression:

The granules for compression obtained in the above (3) were compressed by Cleanpress Correct 12HUK (manufactured by KIKUSUI SEISAKUSHO LTD.) to give uncoated tablets of the formula (b).

(5) Coating:

The uncoated tablets obtained in the above (4) were coated with a coating agent consisting of hydroxypropyl-methylcellulose, titanium oxide, conc. glycerin and carnauba wax by using High Coater HCT30N (manufactured by Freund Industrial Co., Ltd.) under the following conditions so as to control the amount of the coat to 3 mg, thereby FC tablets of the formula (c) were obtained.

FC conditions:
  Temperature for supplying air: 70° C.
  Airflow: 0.6 m$^3$/min.
  Rotation rate of pan: 15 rpm
  Spray pressure: 0.15 MPa
  Liquid flow rate: 5 g/min.
  Distance of gun: 11 cm C. Dissolution Test:

Each 1, 2 or 4 tablets of the film coating tablets obtained by the above method were subjected to the dissolution test according to the Pharmacopoeia of Japan, Method 2, under the following conditions:
  Test solution: Diluted McIlvaine buffer, pH 4.0
  Paddle rotation: 50 rpm
  Volume of test solution: 900 ml The results of the dissolution test are shown below.

TABLE 4

Dissolution test of one FC tablet (10 mg-tablet) (dissolution percentage: %)

| Ex. No. | 0 min | 5 min | 10 min | 15 min | 30 min | 45 min |
|---|---|---|---|---|---|---|
| 1 | 0 | 71 | 86 | 92 | 95 | 97 |

TABLE 5

Dissolution test of 2 FC tablets (10 mg-tablet) (dissolution percentage: %)

| Ex. No. | 0 min | 5 min | 10 min | 15 min | 30 min | 45 min |
|---|---|---|---|---|---|---|
| 1 | 0 | 65 | 83 | 88 | 94 | 96 |

TABLE 6

Dissolution test of 4 FC tablets (10 mg-tablet) (dissolution percentage: %)

| Ex. No. | 0 min | 5 min | 10 min | 15 min | 30 min | 45 min |
|---|---|---|---|---|---|---|
| 1 | 0 | 73 | 83 | 86 | 90 | 92 |

D. Measurement of Solubility of Compound 1:

According to the method disclosed in the Pharmacopoeia of Japan, the solubility (μg/ml) of Compound 1 was measured when treated for 30 minutes under the following conditions.

(1) Conditions for measurement of solubility:
Solvent: Diluted McIlvaine buffer
pH: 3.0, 3.5, 4.0, 4.5, 5.0
Method: HPLC
Temperature: 22 to 23° C.

(2) Results:

TABLE 7

| | pH | | |
|---|---|---|---|
| | 3.0 | 4.0 | 5.0 |
| Solubility (μg/ml) | >20 | 8.2 | 0.7 |

As is shown in Table 7, it was found that the solubility of Compound 1 within 15 minutes measured by the method for determination of solubility disclosed in the Pharmacopoeia of Japan was quite low, and the dissolution speed thereof was also low. On the contrarily, in all of the dissolution tests of 1, 2 or 4 tablets of the present preparation of Example 1, the dissolution of Compound 1 therefrom reached more than 85% within 15 minutes, from which it was shown that the dissolution characteristics of Compound 1 were significantly increased. In addition, the dissolution profile thereof showed a rapid dissolution of Compound 1 from the preparation.

By the way, based on "Guideline for Bioequivalence testing of Oral Solid Dosage Forms with Different Content" of the above-mentioned Notification No. 64, equivalence in dissolution profile of preparations should be judged if the following criteria are met. With respect to preparations showing a rapid dissolution profile, the dissolution percentage reaches 85% or more within 15 minutes, or the dissolution percentage of test preparation is within ±10% of that of the reference preparation.

In the following Examples, the dissolution test was performed on various preparations having different amounts of Compound 1 (e.g., 20 mg-tablet, 40 mg-tablet), and equivalence in dissolution profile thereof was judged by studying whether or not the dissolution percentages thereof within 15 minutes was within ±10% or whether or not the dissolution percentages thereof reach 85% or more within 15 minutes, as compared with the dissolution percentages within 15 minutes in the dissolution test results of 2 or 4 tablets of the 10 mg-tablet of Example 1,.

Examples 2-5

A. Formula of FC Tablet (20 mg-tablet) Containing 20 mg of Compound 1:

In a similar manner to Example 1, granules, uncoated tablets and FC tablets were prepared from the following components.

(a) Formula of granules:

TABLE 8

| | Content (mg) Ex. No. | | | |
|---|---|---|---|---|
| Component | 2 | 3 | 4 | 5 |
| Compound 1 | 20 | 20 | 20 | 20 |
| Lactose | 40 | 39.4 | 38.8 | 37.6 |
| Croscarmellose sodium | 6 | 6 | 6 | 6 |
| Povinyl alcohol | 1.2 | 1.8 | 2.4 | 3.6 |

(b) Formula of uncoated tablets:

TABLE 9

| | Content (mg) Ex. No. | | | |
|---|---|---|---|---|
| Component | 2 | 3 | 4 | 5 |
| Granule of (a) | 67.2 | 67.2 | 67.2 | 67.2 |
| Anhydrous dibasic calcium phosphate | 35 | 35 | 35 | 35 |
| Microcrystalline cellulose | 17 | 17 | 17 | 17 |
| Magnesium stearate | 0.8 | 0.8 | 0.8 | 0.8 |

(c) Formula of FC tablets:

TABLE 10

| | Content (mg) Ex. No. | | | |
|---|---|---|---|---|
| Component | 2 | 3 | 4 | 5 |
| Uncoated tablets of (b) | 120 | 120 | 120 | 120 |
| Hydroxypropylmethylcellulose | 1.95 | 1.95 | 1.95 | 1.95 |
| Titanium oxide | 0.6 | 0.6 | 0.6 | 0.6 |
| Conc. glycerin | 0.45 | 0.45 | 0.45 | 0.45 |
| Carnauba wax | Trace | Trace | Trace | Trace |

B. Preparation Method:

According to the formulae in the above Tables 8, 9 and 10, granules, uncoated tablets and FC tablets were successively prepared in a similar manner to Example 1-B, from which FC tablets having the formula in the above Table 10 (20 mg-tablet) were prepared.

C. Dissolution Test:

With respect to the above FC tablets (20 mg-tablet), the dissolution test was performed in a similar manner to Example 1-C. The results are shown in Table 11.

TABLE 11

| | Dissolution test of one FC tablet (20 mg-tablet) (dissolution percentage: %) | | | | | |
|---|---|---|---|---|---|---|
| Ex. No. | 0 min | 5 min | 10 min | 15 min | 30 min | 45 min |
| 2 | 0 | 64 | 75 | 81 | 90 | 94 |
| 3 | 0 | 61 | 78 | 86 | 96 | 98 |
| 4 | 0 | 61 | 76 | 82 | 89 | 93 |
| 5 | 0 | 59 | 78 | 84 | 90 | 92 |

As is shown in the tablets of the above Examples 2 to 5, when studied by changing the ratio of the water-soluble polymer binder to the slightly water-soluble active ingredient, all preparations having a different ratio thereof showed a rapid dissolution, and it was found that the most effective ratio thereof was within the range of 6 to 18%.

The dissolution percentages within 15 minutes of these preparations was within ±10% of that of 2 tablets of the 10 mg-tablet of Example 1, which meet the acceptance criteria for equivalence of dissolution profile as defined in the above Guideline. Therefore, it is apparent that all of the preparations of Examples 2 to 5 are equivalent in dissolution profile.

Examples 6-10

A. Formula of FC Tablets (20 mg-tablet) Containing 20 mg of Compound 1:

In a similar manner to Example 1, granules, uncoated tablets and FC tablets were prepared from the following components.

(a) Formula of granules:

TABLE 12

| | Content (mg) Ex. No. | | | | |
|---|---|---|---|---|---|
| Component | 6 | 7 | 8 | 9 | 10 |
| Compound 1 | 20 | 20 | 20 | 20 | 20 |
| Lactose | 37.6 | 37.6 | 37.6 | 37.6 | 37.6 |
| Croscarmellose sodium | 6 | 6 | 6 | 6 | 6 |
| Hydroxypropylmethylcellulose | 2.4 | 2.4 | 2.4 | 2.4 | 2.4 |

(b) Formula of uncoated tablets:

TABLE 13

| | Content (mg) Ex. No. | | | | |
|---|---|---|---|---|---|
| Component | 6 | 7 | 8 | 9 | 10 |
| Granule of (a) | 67.2 | 67.2 | 67.2 | 67.2 | 67.2 |
| Lactose | 52 | | 35 | 17 | |
| Microcrystalline cellulose | | 52 | 17 | | 17 |
| Anhydrous dibasic calcium phosphate | | | | 35 | 35 |
| Magnesium stearate | 0.8 | 0.8 | 0.8 | 0.8 | 0.8 |

(c) Formula of FC tablets:

TABLE 14

| | Content (mg) Ex. No. | | | | |
|---|---|---|---|---|---|
| Component | 6 | 7 | 8 | 9 | 10 |
| Uncoated tablets of (b) | 120 | 120 | 120 | 120 | 120 |
| Hydroxypropylmethylcellulose | 1.95 | 1.95 | 1.95 | 1.95 | 1.95 |
| Titanium oxide | 0.6 | 0.6 | 0.6 | 0.6 | 0.6 |
| Conc. glycerin | 0.45 | 0.45 | 0.45 | 0.45 | 0.45 |
| Carnauba wax | Trace | Trace | Trace | Trace | Trace |

B. Preparation Method:

According to the formulae in the above Tables 12, 13 and 14, granules, uncoated tablets and FC tablets were successively prepared in a similar manner to Example 1-B, from which FC tablets having the formula in the above Table 14 (20 mg-tablet) were prepared, respectively.

C. Dissolution Test:

With respect to the above FC tablets (20 mg-tablet), the dissolution test was performed in a similar manner to Example 1-C. The results are shown in Table 15.

TABLE 15

| | Dissolution test of one FC tablet (20 mg-tablet) (dissolution percentage: %) | | | | | |
|---|---|---|---|---|---|---|
| Ex. No. | 0 min | 5 min | 10 min | 15 min | 30 min | 45 min |
| 6 | 0 | 54 | 77 | 85 | 91 | 92 |
| 7 | 0 | 29 | 67 | 84 | 90 | 93 |
| 8 | 0 | 46 | 75 | 83 | 88 | 90 |
| 9 | 0 | 64 | 76 | 80 | 85 | 89 |
| 10 | 0 | 63 | 75 | 80 | 84 | 86 |

As shown in the data of the tablets of the above Examples 6-10, all of the present preparations wherein the kinds of a second disintegrant and the mixing ratio thereof are varied showed a rapid dissolution profile. The dissolution percentage within 15 minutes of these preparations was all within ±10% of that of 2 tablets of the 10 mg-tablet obtained in the above Example 1, which means that the present preparations can be equivalent in dissolution profile.

Examples 11-14

A. Formula of FC Tablets (20 mg-tablet) Containing 20 mg of Compound 1:

In a similar manner to Example 1, granules, uncoated tablets and FC tablets were prepared from the following components.

(a) Formula of granules:

TABLE 16

| | Content (mg) Ex. No. | | | |
|---|---|---|---|---|
| Component | 11 | 12 | 13 | 14 |
| Compound 1 | 20 | 20 | 20 | 20 |
| Lactose | 37.6 | 37.6 | 37.6 | 37.6 |
| Croscarmellose sodium | 6 | 6 | 6 | 6 |
| Hydroxypropylcellulose | 2.4 | 2.4 | 2.4 | 2.4 |

(b) Formula of uncoated tablets:

TABLE 17

| | Content (mg) Ex. No. | | | |
|---|---|---|---|---|
| Component | 11 | 12 | 13 | 14 |
| Granule of (a) | 67.2 | 67.2 | 67.2 | 67.2 |
| Lactose | 52 | | 35 | 17 |
| Microcrystalline cellulose | | 52 | 17 | |
| Anhydrous dibasic calcium phosphate | | | | 35 |
| Magnesium stearate | 0.8 | 0.8 | 0.8 | 0.8 |

(c) Formula of FC tablets:

TABLE 18

| | Content (mg) Ex. No. | | | |
|---|---|---|---|---|
| Component | 11 | 12 | 13 | 14 |
| Uncoated tablets of (b) | 120 | 120 | 120 | 120 |
| Hydroxypropylmethylcellulose | 1.95 | 1.95 | 1.95 | 1.95 |
| Titanium oxide | 0.6 | 0.6 | 0.6 | 0.6 |
| Conc. glycerin | 0.45 | 0.45 | 0.45 | 0.45 |
| Carnauba wax | Trace | Trace | Trace | Trace |

B. Preparation Method:

According to the formulae in the above Tables 16, 17 and 18, granules, uncoated tablets and FC tablets were successively prepared in a similar manner to Example 1-B, from which FC tablets having the formula in the above Table 19 (20 mg-tablet) were prepared, respectively.

C. Dissolution Test:

With respect to the above FC tablets (20 mg-tablet), the dissolution test was performed in a similar manner to Example 1-C. The results are shown in Table 19.

TABLE 19

| Dissolution test of one FC tablet (20 mg-tablet) (dissolution percentage: %) | | | | | | |
|---|---|---|---|---|---|---|
| Ex. No. | 0 min | 5 min | 10 min | 15 min | 30 min | 45 min |
| 11 | 0 | 51 | 76 | 84 | 91 | 93 |
| 12 | 0 | 41 | 78 | 86 | 93 | 96 |
| 13 | 0 | 48 | 74 | 82 | 89 | 92 |
| 14 | 0 | 54 | 72 | 78 | 85 | 88 |

As shown in the data of the tablets of the above Examples 11-14, all of the preparations of the present invention wherein the kinds of a water-soluble excipient for granules were changed, and the kinds of the second disintegrant and the mixing ratio thereof were changed showed a rapid dissolution profile. The dissolution percentage within 15 minutes of these preparations were all within ±10% of that of 2 tablets of the 10 mg-tablet in the above Example 1, which means that the present preparations can be equivalent in dissolution profile.

Examples 15-18

A. Formula of FC Tablets (20 mg-tablet) Containing 20 mg of Compound 1:

In a similar manner to Example 1, granules, uncoated tablets and FC tablets were prepared from the following components.

(a) Formula of granules:

TABLE 20

| | Content (mg) Ex. No. | | | |
|---|---|---|---|---|
| Component | 15 | 16 | 17 | 18 |
| Compound 1 | 20 | 20 | 20 | 20 |
| Lactose | 37.6 | 37.6 | 37.6 | 37.6 |
| Croscarmellose sodium | 6 | 6 | 6 | 6 |
| Povidone (polyvinylpyrrolidone) | 2.4 | 2.4 | 2.4 | 2.4 |

(b) Formula of uncoated tablets:

TABLE 21

| | Content (mg) Ex. No. | | | |
|---|---|---|---|---|
| Component | 15 | 16 | 17 | 18 |
| Granule of (a) | 67.2 | 67.2 | 67.2 | 67.2 |
| Lactose | 52 | 35 | 17 | 35 |
| Microcrystalline cellulose | | | 17 | 35 |
| Anhydrous dibasic calcium phosphate | | | | 17 |
| Magnesium stearate | 0.8 | 0.8 | 0.8 | 0.8 |

(c) Formula of FC tablets:

TABLE 22

| | Content (mg) Ex. No. | | | |
|---|---|---|---|---|
| Component | 15 | 16 | 17 | 18 |
| Uncoated tablets of (b) | 120 | 120 | 120 | 120 |
| Hydroxypropylmethylcellulose | 1.95 | 1.95 | 1.95 | 1.95 |
| Titanium oxide | 0.6 | 0.6 | 0.6 | 0.6 |
| Conc. glycerin | 0.45 | 0.45 | 0.45 | 0.45 |
| Carnauba wax | Trace | Trace | Trace | Trace |

B. Preparation Method:

According to the formulae in the above Tables 20, 21 and 22, granules, uncoated tablets and FC tablets were successively prepared in a similar manner to Example 1-B, from which FC tablets having the Formula in the above Table 22 (20 mg-tablet) were prepared, respectively.

C. Dissolution Test:

With respect to the above FC tablets (20 mg-tablet), the dissolution test was performed in a similar manner to Example 1-C. The results are shown in Table 23.

TABLE 23

| Dissolution test of one FC tablet (20 mg-tablet) (dissolution percentage: %) | | | | | | |
|---|---|---|---|---|---|---|
| Ex. No. | 0 min | 5 min | 10 min | 15 min | 30 min | 45 min |
| 15 | 0 | 53 | 75 | 84 | 92 | 94 |
| 16 | 0 | 45 | 74 | 81 | 89 | 92 |
| 17 | 0 | 40 | 72 | 80 | 88 | 91 |
| 18 | 0 | 58 | 76 | 83 | 92 | 94 |

As shown in the data of the tablets of the above Examples 15-18, all of the preparations of the present invention wherein the kinds of a water-soluble excipient for the granules were changed, and the kinds of the second disintegrant and the mixing ratio thereof were changed showed a rapid dissolution profile. The dissolution percentages within 15 minutes of these preparations were all within ±10% of that of 2 tablets of the 10 mg-tablet in the above Example 1, which means that the present preparations can be equivalent in dissolution profile.

Example 19

A. Formula of FC Tablets (20 mg-tablet) Containing 20 mg of Compound 1:

In a similar manner to Example 1, granules, uncoated tablets and FC tablets were prepared from the following components.

(a) Formula of granules:

TABLE 24

| Component | Content (mg) Ex. No. 19 |
|---|---|
| Compound 1 | 20 |
| D-Mannitol | 94 |
| Croscarmellose sodium | 8 |
| Hydroxypropylmethylcellulose | 5 |

(b) Formula of uncoated tablets:

TABLE 25

| Component | Content (mg) Ex. No. 19 |
|---|---|
| Granules of (a) | 127 |
| Lactose | 31 |
| Magnesium stearate | 2 |

(c) Formula of FC tablets:

TABLE 26

| Component | Content (mg) Ex. No. 19 |
|---|---|
| Uncoated tablets of (a) | 160 |
| Hydroxypropylmethylcellulose | 1.95 |
| Titanium oxide | 0.6 |
| Polyethyleneglycol | 0.45 |
| Carnauba wax | Trace |

B. Preparation Method:

According to the formulae in the above Tables 24, 25 and 26, granules, uncoated tablets and FC tablets were successively prepared in a similar manner to Example 1-B, from which FC tablets having the formula in the above Table 26 (20 mg-tablet) were prepared, respectively.

C. Dissolution Test:

With respect to the above FC tablets (20 mg-tablet), the dissolution test was performed in a similar manner to Example 1-C. The results are shown in Table 27.

TABLE 27

| Dissolution test of one FC tablet (20 mg-tablet) (dissolution percentage: %) | | | | | |
|---|---|---|---|---|---|
| Ex. No. | 0 min | 10 min | 15 min | 30 min | 45 min |
| 19 | 0 | 89 | 92 | 95 | 97 |

As is shown in the data of the tablets of the above Example 19, the preparation of the present invention wherein the kinds of water-soluble excipient for granules were changed, and the kinds of the second disintegrant and the mixing ratio thereof were changed showed a rapid dissolution profile. The dissolution percentages within 15 minutes of the present preparations were all within ±10% of that of 2 tablets of the 10 mg-tablet in the above Example 1, which means that the present preparations can be equivalent in dissolution profile.

Examples 20-23

A. Formula of FC Tablets (40 mg-tablet) Containing 40 mg of Compound 1:

In a similar manner to Example 1, granules, uncoated tablets and FC tablets were prepared from the following components.

(a) Formula of granules:

TABLE 28

| | Content (mg) Ex. No. | | | |
|---|---|---|---|---|
| Component | 20 | 21 | 22 | 23 |
| Compound 1 | 40 | 40 | 40 | 40 |
| D-Mannitol | 188 | 188 | 132 | 132 |
| Corn starch | — | — | 56 | 56 |
| Croscarmellose sodium | 16 | 16 | 12 | 12 |
| Hydroxypropylmethylcellulose | 8 | 12 | 8 | 8 |

(b) Formula of uncoated tablets:

TABLE 29

| | Content (mg) Ex. No. | | | |
|---|---|---|---|---|
| Component | 20 | 21 | 22 | 23 |
| Granule of (a) | 252 | 256 | 248 | 248 |
| Lactose | 80 | 60 | 150 | — |
| Microcrystalline cellulose | — | — | — | 150 |
| Magnesium stearate | 4 | 4 | 2 | 2 |

(c) Formula of FC tablets:

TABLE 30

| | Content (mg) Ex. No. | | | |
|---|---|---|---|---|
| Component | 20 | 21 | 22 | 23 |
| Uncoated tablet of (b) | 336 | 320 | 400 | 400 |
| Hydroxypropylmethylcellulose | 2.6 | 2.6 | — | — |
| Titanium oxide | 0.8 | 0.8 | — | — |
| Polyethyleneglycol | 0.6 | 0.6 | — | — |
| Carnauba wax | Trace | Trace | — | — |

B. Preparation Method:

According to the formulae in the above Tables 28, 29 and 30, granules, uncoated tablets or FC tablets were successively prepared in a similar manner to Example 1-B, from which uncoated tablets or FC tablets having the formulae in the above Tables 29 and 30 (40 mg-tablet) were prepared, respectively.

C. Dissolution Test:

With respect to the above uncoated tablets (Examples 22 and 23) and FC tablets (Examples 20 and 21), the dissolution test was performed in a similar manner to Example 1-C. The results are shown in Table 31.

TABLE 31

Dissolution test of one uncoated tablet or one FC tablet (dissolution percentage: %)

| Ex. No. | 0 min | 10 min | 15 min | 30 min | 45 min |
|---|---|---|---|---|---|
| 20 | 0 | 82 | 90 | 94 | 96 |
| 21 | 0 | 83 | 92 | 97 | 97 |
| 22 | 0 | 85 | 94 | 97 | 98 |
| 23 | 0 | 83 | 86 | 87 | 87 |

As is shown in the data of the tablets of the above Examples 20-23, all of the preparations of the present invention wherein the components of granules were changed, and the kinds of the second disintegrant and the mixing ratio thereof were changed and further the amount of the active ingredient was changed to 40 mg per tablet showed a rapid dissolution profile. The dissolution percentages within 15 minutes of the present preparations were all within ±10% of that of 4 tablets of the 10 mg-tablet in the above Example 1, which means that the present preparations can be equivalent in dissolution profile.

Examples 24-27

A. Formula of Uncoated Tablets (40 mg-tablet) Containing 40 mg of Compound 1:

In a similar manner to Example 1, uncoated tablets were prepared from the following components. Formula of uncoated tablets:

TABLE 32

| | Content (mg) Ex. No. | | | |
|---|---|---|---|---|
| Component | 24 | 25 | 26 | 27 |
| Compound 1 | 40 | 40 | 40 | 40 |
| D-Mannitol | 132 | 255 | 188 | 325 |
| Corn starch | 56 | 70 | — | — |
| Croscarmellose sodium | 12 | 20 | 12.5 | 20 |
| Hydroxypropylmethylcellulose | 8 | 12 | 7.5 | 12 |
| Magnesium stearate | 2 | 3 | 2 | 3 |

B. Preparation Method:

The composition of Example 24 as shown in the above Table 32 was prepared by the following method to give uncoated tablets. The compositions of Examples 25, 26 and 27 were also prepared by the following method.

(1) Preparation of a binding solution:

Hydroxypropylmethylcellulose (12 g) as a water-soluble polymer binder was dissolved in purified water (228 g) to give a binding solution.

(2) Granulation:

Compound 1 (60 g), D-mannitol (198 g) as a water-soluble excipient, and croscarmellose sodium (84 g) and corn starch (18 g) as first disintegrants were charged into a fluid bed granulator (Multiplex MP-01 manufactured by Pawrex Corporation), and the mixture was granulated by spray granulation under the following conditions using the binding solution obtained in the above (1) to give the granules of Example 24.

Conditions for granulation:

Temperature for supplying air: 70° C.

Airflow: 50 $m^3$/hr

Spray speed: 10 g/min.

Diameter of spray nozzle: 1.2 mm

Spray pressure: 0.15 $MPa/cm^2$

Gun position: the lower stand (3) Blending:

To the granules obtained in the above (2) was added magnesium stearate (3 g, said amount being changed depending on the yield) as a lubricant, and the mixture was blended at 40 rpm for 5 minutes.

(4) Compression:

The granules for compression obtained in the above (3) were compressed by Clearpress Correct 12HUK (manufactured by KIKUSUI SEISAKUSHO LTD.) under the following conditions to give uncoated tablets of the formula in Table 32.

C. Dissolution Test:

With respect to the above uncoated tablets (40 mg-tablet), the dissolution test was performed in a similar manner to Example 1-C. The results are shown in Table 33.

TABLE 33

Dissolution test of one uncoated tablet (40 mg-tablet) (dissolution percentage: %)

| Ex. No. | 0 min | 10 min | 15 min | 30 min | 45 min |
|---|---|---|---|---|---|
| 24 | 0 | 74 | 87 | 91 | 98 |
| 25 | 0 | 90 | 98 | 99 | 100 |
| 26 | 0 | 87 | 95 | 97 | 98 |
| 27 | 0 | 84 | 94 | 97 | 98 |

As is shown in the data of the tablets of the above Examples 24-27, all of the preparations of the present invention wherein the components for granules and the mixing ratio thereof were changed showed a rapid dissolution profile. The dissolution percentages within 15 minutes of the present preparations were all within ±10% of that of 4 tablets of the 10 mg-tablet in the above Example 1, or 85% or more, which means that the present preparations can be equivalent in dissolution profile.

Example 28

A. Formula of Granules, Uncoated Tablets and FC Tablets (40 mg-tablet) Containing 40 mg of Compound 1:

In a similar manner to Example 1, granules, uncoated tablets and FC tablets were prepared from the following components.

(a) Formula of granules:

TABLE 34

| Component | Content (mg) Ex. No. 28 |
|---|---|
| Compound 1 | 40 |
| D-Mannitol | 188 |
| Croscarmellose sodium | 16 |
| Hydroxypropylmethylcellulose | 10 |

(b) Formula of uncoated tablets:

TABLE 35

| Component | Content (mg) Ex. No. 28 |
|---|---|
| Granules of (a) | 254 |
| Lactose | 62 |
| Magnesium stearate | 4 |

(c) Formula of FC tablets:

TABLE 36

| Component | Content (mg) Ex. No. 28 |
|---|---|
| Granule of (b) | 320 |
| Hydroxypropylmethylcellulose | 2.6 |
| Titanium oxide | 0.8 |
| Polyethyleneglycol | 0.6 |
| Carnauba wax | Trace |

B. Preparation Method:
(1) Preparation of a binding solution:
Hydroxypropylmethylcellulose (30 g) as a water-soluble polymer binder was dissolved in purified water (570 g) to give a binding solution.
(2) Granulation:
Compound A (120 g), D-mannitol (564 g) and croscarmellose sodium (48 g) as a first disintegrant were charged to a fluid bed granulator (Multiplex MP-01 manufactured by Pawrex Corporation), and the mixture was granulated by spray granulation under the following conditions using the binding solution obtained in the above (1) to give granules of the Formula (a).

Conditions for granulation:
Temperature for supplying air: 60° C.
Airflow: 50 m³/hr
Spray speed: 10 g/min.
Diameter of spray nozzle: 1.2 mm
Spray pressure: 0.12 MPa/cm²
Gun position: the middle stand
(3) Mixing of the granules and a second disintegrant:
To the granules (723.9 g) obtained in the above (2) was added lactose (176.7 g) as a second disintegrant, and the mixture was mixed using a compact. V Blender (manufactured by Tsutsui Rikagaku Kikai Co., Ltd.). at 40 rpm for 15 minutes. Subsequently, the mixture was further milled (2350 rpm, knife, 16 mesh) using Fits Mill (manufactured by HOSOKAWAMICRON CORPORATION). After mixing, magnesium stearate (11.4 g, said amount being changed depending on the yield) as a lubricant was added thereto and mixed (40 rpm, 5 minutes).

(4) Compression:
The granules for compression obtained in the above (3) were compressed using Cleanpress Correct 12HUK (manufactured by KIKUSUI SEISAKUSHO LTD.) under the following conditions to give uncoated tablets of the Formula (b).
(5) Coating:
The uncoated tablets obtained in the above (4) were coated with a coating agent consisting of hydroxypropyl-methylcellulose, titanium oxide, polyethylene glycol and carnauba wax by High Coater HCT30N (manufactured by Freund Industrial Co., Ltd.) under the following conditions so that the amount of the coat is controlled to 3 mg, and give FC tablets of the Formula (c).

FC conditions:
Temperature for supplying air: 80° C.
Airflow: 0.6 m³/min.
Rotation rate of pan: 25 rpm
Spray pressure: 0.15 MPa
Liquid flow rate: 5 g/min.
Distance of gun: 11 cm C. Dissolution Test:
With respect to the above FC tablets (40 mg-tablet), the dissolution test was performed in a similar manner to Example 1-C. The results are shown in Table 37. The results of the dissolution test:

TABLE 37

| Ex. No. | 10 min | 15 min | 30 min | 45 min |
|---|---|---|---|---|
| 28 | 81 | 90 | 94 | 96 |

Comparative Example 1

Dissolution Characteristics of a Preparation Having a Standard Formula Prepared by a Standard Method
(1)

In a comparative example for evaluating the dissolution characteristics of preparations having a standard formula and prepared by a standard method, the dissolution characteristics of the tablets prepared by a conventional technique were evaluated.

A. Preparation of FC Tablets (20 mg-tablet):
From the following formula, a slightly water-soluble active ingredient, lactose as a representative water-soluble excipient, and corn starch as a disintegrant were charged into a fluid bed granulator, and the mixture was granulated by spay granulation using a water-soluble polymer solution. Magnesium stearate was blended with the resulting granules, and the mixture was compressed to give uncoated tablets, which were further subjected to film coating to give FC tablets (20 mg-tablet).

(a) Formula of uncoated tablets:

TABLE 38

| Component | Content (mg) |
|---|---|
| Compound 1 | 20 |
| Lactose | 70.0 |
| Corn starch | 22.0 |
| Croscarmellose sodium | 6 |
| Polyvinyl alcohol | 1.2 |
| Magnesium stearate | 0.8 |

(b) Formula of FC tablets:

TABLE 39

| Component | Content (mg) |
|---|---|
| Uncoated tablet of (a) | 120 |
| Hydroxypropylmethylcellulose | 1.95 |
| Titanium oxide | 0.6 |
| Conc. glycerin | 0.45 |
| Carnauba wax | Trace |

B. Dissolution test:

With respect to the FC tablets (20 mg-tablet) obtained in the above Comparative Example 1, the dissolution test was performed in a similar manner to Example 1-C. The results are shown in Table 40.

TABLE 40

| | Dissolution test of one FC tablet (20 mg-tablet) (dissolution percentage: %) | | | | | |
|---|---|---|---|---|---|---|
| Com. Ex. | 0 min | 5 min | 10 min | 15 min | 30 min | 45 min |
| 1 | 0 | 35 | 56 | 68 | 71 | 86 |

As is shown in the above dissolution test, the dissolution percentage within 15 minutes of the FC tablet (20 mg-tablet) obtained in Comparative Example 1, which was prepared by a conventional method, was merely 68%, and even the dissolution percentage within 30 minutes was still low such as merely 71%, which was significantly inferior to the dissolution characteristics of the FC tablets (20 mg-tablet) of Examples 2-19 of the present invention. Further, the dissolution percentage within 15 minutes of the FC tablet of Comparative Example 1 was lower by more than 20% than that of 2 tablets of the 10 mg-tablet of Example 1, and further the dissolution profile thereof was quite different.

Comparative Example 2

Dissolution Characteristics of a Preparation Having a Standard Formula Prepared by a Standard Method (2)

In Comparative Example 2, the dissolution characteristics of FC tablet (20 mg-tablet) prepared by a conventional method were evaluated.

A. Preparation of FC Tablet (20 mg-tablet):

From the following components, a slightly water-soluble active ingredient, microcrystalline cellulose and anhydrous dibasic calcium phosphate as representative disintegrants were mixed in a similar manner to Example 1 as mentioned above, and thereto was added magnesium stearate. The mixture was compressed to give uncoated tablets, which were further subjected to film coating to give FC tablets (20 mg-tablet).

(a) Formula of uncoated tablets:

TABLE 41

| Component | Content (mg) |
|---|---|
| Compound 1 | 20 |
| Microcrystalline cellulose | 70.0 |
| Anhydrous dibasic calcium phosphate | 23.2 |
| Magnesium stearate | 0.8 |

(b) Formula of FC tablets

TABLE 42

| Component | Content (mg) |
|---|---|
| Uncoated tablet of (a) | 120 |
| Hydroxypropylmethylcellulose | 1.95 |
| Titanium oxide | 0.6 |
| Conc. glycerin | 0.45 |
| Carnauba wax | Trace |

B. Dissolution test:

With respect to the FC tablets (20 mg-tablet) obtained in the above Comparative Example 2, the dissolution test was performed in a similar manner to Example 1-C. The results are shown in Table 43.

TABLE 43

| | Dissolution test of one FC tablet (20 mg-tablet) (dissolution percentage: %) | | | | | |
|---|---|---|---|---|---|---|
| Com. Ex. | 0 min | 5 min | 10 min | 15 min | 30 min | 45 min |
| 2 | 0 | 42 | 57 | 63 | 70 | 75 |

As is shown in the above dissolution test, the dissolution percentage within 15 minutes of the FC tablets (20 mg-tablet) obtained by a conventional method in Comparative Example 2 was merely 63%, and even the dissolution percentage within 30 minutes was still low such as merely 70%, which is significantly inferior to the dissolution characteristics of the FC tablets (20 mg-tablet) of Examples 2-19 of the present invention. Further, the dissolution percentage within 15 minutes is lower by about 25% than that of 2 tablets of the 10 mg-tablet of Example 1, and the dissolution profile thereof is quite different.

Comparative Example 3

Dissolution Characteristics of a Preparation Having a Standard Formula Prepared by a Standard Method (3)

In Comparative Example 3, the dissolution characteristics of FC tablet (40 mg-tablet) prepared by a conventional method were evaluated.

A. Preparation of FC Tablet (40 mg-tablet):

According to the following formula, mannitol as a representative water-soluble excipient was charged into a fluid bed granulator, and the mixture was granulated by spay granulation using a binding solution wherein a slightly water-soluble active ingredient was dispersed and suspended in a water-soluble polymer binder solution. The resulting granules were blended with magnesium stearate, and the mixture was compressed to give uncoated tablets, which were further subjected to film coating to give FC tablets (40 mg-tablet).

(a) Formula of uncoated tablets:

TABLE 44

| Component | Content (mg) |
|---|---|
| Compound 1 | 40 |
| Mannitol | 77.0 |
| Croscarmellose sodium | 12 |
| Polyvinyl alcohol | 4.8 |
| Magnesium stearate | 0.9 |

(b) Formula of FC tablets

TABLE 45

| Component | Content (mg) |
| --- | --- |
| Uncoated tablet of (a) | 134.7 |
| Hydroxypropylmethylcellulose | 1.95 |
| Titanium oxide | 0.6 |
| Conc. glycerin | 0.45 |
| Carnauba wax | Trace |

B. Dissolution Test:

With the FC tablets (40 mg-tablet) obtained in the above Comparative Example 3, the dissolution test was performed in a similar manner to Example 1-C. The results are shown in Table 46.

TABLE 46

| Dissolution test of one FC tablet (40 mg-tablet) (dissolution percentage: %) | | | | | | |
| --- | --- | --- | --- | --- | --- | --- |
| Com. Ex. | 0 min | 5 min | 10 min | 15 min | 30 min | 45 min |
| 3 | 0 | 26 | 53 | 74 | 84 | 88 |

As is shown in the above dissolution test, the dissolution percentage within 15 minutes of the FC tablets (40 mg-tablet) obtained by a conventional method in Comparative Example 3 was merely 74%, and even the dissolution percentage within 30 minutes was still 84%, which is significantly inferior to the dissolution characteristics of the FC tablets of Examples 20-28 (40 mg-tablet) of the present invention. Further, the dissolution percentage within 15 minutes was lower by more than 10% than that of 4 tablets of the 10 mg-tablet of Example 1, and the dissolution profile thereof was different.

As explained in the above, the preparations of Comparative Examples 1-3 prepared by a conventional method were inferior in dissolution characteristics, and did not show a desired dissolution profile. Thus, by the conventional method, the object of the present invention, i.e., a desired oral preparation being equivalent in dissolution profile at different amounts of an active ingredient, can not be achieved.

INDUSTRIAL APPLICABILITY

The oral preparation with good disintegration of the present invention containing a slightly water-soluble compound as an active ingredient shows an excellent dissolution characteristic of said active ingredient from the preparation in the digestive tract, and these preparations show equivalent dissolution profile at different amounts of the active ingredient. Therefore, according to the present invention, by preparing various preparations having different amounts of an active ingredient, the selection of the most suitable medicament for each patient can be made possible, by which highly useful medicament in the clinical field can be provided.

The invention claimed is:

1. A rapidly disintegrating oral preparation comprising:
   i) granules, said granules comprising:
   a water-soluble excipient selected from either one or both of lactose and mannitol;
   a first disintegrant selected from one or more of corn starch, microcrystalline cellulose, low substituted hydroxypropylcellulose, carmellose, carmellose calcium, carmellose sodium, croscarmellose sodium, carboxymethyl starch sodium and crosspovidone;
   a water-soluble polymer binder selected from one or more of hydroxypropylcellulose, hydroxypropylmethylcellulose, polyvinylpyrrolidone, and partially saponified polyvinyl alcohol; and
   an active ingredient that is N-[4-[4-(1,2-benzisothiazol-3-yl)-1-piperazinyl]-(2R,3R)-2,3-tetramethylenebutyl]-(1'R,2'S,3'R,4'S)-2,3-bicyclo[2.2.1]heptanedicarboximide hydrochloride; and
   ii) a second disintegrant selected from one or more of lactose, anhydrous dibasic calcium phosphate, dibasic calcium phosphate, microcrystalline cellulose, low substituted hydroxypropylcellulose, carmellose, carmellose calcium, carmellose sodium, croscarmellose sodium, carboxymethyl starch sodium, and crosspovidone;
   wherein said granules are mixed in said second disintegrant, and
   wherein said active ingredient is contained in an amount of 5 to 40 mg, and
   wherein said water-soluble excipient is contained an amount of 200 to 2000% by weight of the active ingredient, and
   wherein said first disintegrant is contained in an amount of 5 to 300% by weight to the weight of the active ingredient, and
   wherein said water-soluble polymer binder is contained in an amount of about 1 to 5% by weight to the total weight of said preparation, and
   wherein said second disintegrant is contained in amount of 20 to 1200% by weight to the weight of the granule.

2. The rapidly disintegrating oral preparation of claim 1, in which the water-soluble excipient is lactose.

3. The rapidly disintegrating oral preparation of claim 1, in which the water-soluble excipient is mannitol.

4. The rapidly disintegrating oral preparation of claim 3, in which the dissolution rate of the N-[4-[4-(1,2-benzisothiazol-3-yl)-1-piperazinyl]-(2R,3R)-2,3-tetramethylenebutyl]-(1'R,2'S,3'R,4'S)-2,3-bicyclo[2.2.1]heptanedicarboximide hydrochloride in diluted McIlvaine buffer (pH: 4.0) is at least 85% within 15 minutes.

5. The rapidly disintegrating oral preparation of claim 2, in which the dissolution rate of the N-[4-[4-(1,2-benzisothiazol-3-yl)-1-piperazinyl]-(2R,3R)-2,3-tetramethylenebutyl]-(1'R,2'S,3'R,4'S)-2,3-bicyclo[2.2.1]heptanedicarboximide hydrochloride in diluted McIlvaine buffer (pH: 4.0) is at least 80% within 15 minutes.

6. The rapidly disintegrating oral preparation of claim 3, in which the mannitol is contained in an amount of 250 to 1200% by weight based on the weight of the active ingredient.

7. The rapidly disintegrating oral preparation of claim 1, in which the first disintegrant is contained in an amount of 30 to 150% by weight based on the weight of the active ingredient.

8. The rapidly disintegrating oral preparation of claim 1, that dissolves rapidly in a solution of pH from 3 to 5.

9. The rapidly disintegrating oral preparation of claim 1, in which said granule is prepared by fluidized bed granulation.

10. The rapidly disintegrating oral preparation of claim 1, wherein said granule has a layered structure comprising an internal layer of said first disintegrant and a water-soluble excipient, upon which is set a layer comprising said active ingredient.

11. The rapidly disintegrating oral preparation of claim 1, wherein the dissolution percentage of said oral preparation is at least 59% after 5 minutes and at least 92% after 45 minutes.

* * * * *